United States Patent
Heimann et al.

(10) Patent No.: US 8,921,738 B2
(45) Date of Patent: Dec. 30, 2014

(54) GAS SENSOR HEATING DEVICE INSULATION

(75) Inventors: Detlef Heimann, Gerlingen (DE); Thomas Wahl, Pforzheim (DE); Lothar Diehl, Gerlingen (DE); Thomas Moser, Schwieberdingen (DE); Stefan Rodewald, Ditzingen (DE)

(73) Assignee: Robert Bosch GmbH, Stuttgart (DE)

( * ) Notice: Subject to any disclaimer, the term of this patent is extended or adjusted under 35 U.S.C. 154(b) by 2533 days.

(21) Appl. No.: 10/515,541

(22) PCT Filed: Apr. 29, 2003

(86) PCT No.: PCT/DE03/01372
§ 371 (c)(1),
(2), (4) Date: Aug. 18, 2005

(87) PCT Pub. No.: WO03/100409
PCT Pub. Date: Dec. 4, 2003

(65) Prior Publication Data
US 2006/0091008 A1     May 4, 2006

(30) Foreign Application Priority Data
May 23, 2002 (DE) .................................. 102 22 791

(51) Int. Cl.
    *B60L 1/02*           (2006.01)
    *G01N 27/407*        (2006.01)
    *G01N 27/406*        (2006.01)

(52) U.S. Cl.
    CPC ........ *G01N 27/4071* (2013.01); *G01N 27/4067* (2013.01)

USPC ........................................................ 219/202

(58) Field of Classification Search
USPC .......... 219/202, 543, 548; 204/408, 426, 427, 204/429, 431; 73/23.32
See application file for complete search history.

(56) References Cited

U.S. PATENT DOCUMENTS

| | | | | |
|---|---|---|---|---|
| 4,294,679 A | * | 10/1981 | Maurer et al. | 204/426 |
| 4,305,803 A | * | 12/1981 | Beyer et al. | 204/426 |
| 4,498,968 A | * | 2/1985 | Yamada et al. | 204/412 |
| 4,559,126 A | * | 12/1985 | Mase et al. | 204/425 |
| 4,720,394 A | * | 1/1988 | Kojima et al. | 427/102 |

(Continued)

FOREIGN PATENT DOCUMENTS

| | | | |
|---|---|---|---|
| DE | 198 34 276 | 2/2000 | |
| DE | 198 53 601 | 5/2000 | |
| EP | 0845669 | 6/1998 | |
| WO | WO 9830894 A1 * | 7/1998 | ........... G01N 27/407 |

OTHER PUBLICATIONS

R. Jurgen, *Automotive Electronics Handbook*, Ed. 1999, McGraw-Hill, Section 7.

*Primary Examiner* — Dana Ross
*Assistant Examiner* — Joseph Iskra
(74) *Attorney, Agent, or Firm* — Kenyon & Kenyon LLP

(57) ABSTRACT

A heating device for a sensor element of a gas sensor, in particular for use in exhaust gas analysis of internal combustion engines, has a heating element, which has an electrical resistor layer. The heating element is electrically insulated from at least one solid electrolyte layer by a layer containing barium and/or strontium and/or calcium. For this purpose, the heating element is embedded in a first insulator, which is adjoined by a second insulator. The first insulator has a higher barium and/or strontium and/or calcium content (expressed in weight percentage) than the second insulator.

15 Claims, 1 Drawing Sheet

(56) References Cited

U.S. PATENT DOCUMENTS

| | | | |
|---|---|---|---|
| 5,006,221 A * | 4/1991 | Uchikawa et al. | 204/426 |
| 5,169,513 A * | 12/1992 | Mase et al. | 204/429 |
| 5,298,147 A * | 3/1994 | Nakae et al. | 204/424 |
| 5,447,618 A * | 9/1995 | Sugiyama et al. | 204/426 |
| 5,562,811 A * | 10/1996 | Lenfers | 204/408 |
| 5,670,032 A | 9/1997 | Friese et al. | |
| 5,753,893 A * | 5/1998 | Noda et al. | 219/548 |
| 5,773,894 A * | 6/1998 | Friese et al. | 257/760 |
| 5,849,165 A * | 12/1998 | Kojima et al. | 204/429 |
| 5,997,707 A * | 12/1999 | Kato et al. | 204/425 |
| 6,344,119 B2 * | 2/2002 | Kato et al. | 204/425 |
| 6,350,357 B1 | 2/2002 | Heussner et al. | |
| 6,367,309 B1 * | 4/2002 | Diehl et al. | 73/23.32 |
| 6,676,817 B2 * | 1/2004 | Noda et al. | 204/424 |
| 2001/0008211 A1 * | 7/2001 | Kato et al. | 204/426 |
| 2003/0034247 A1 * | 2/2003 | Noda et al. | 204/424 |

\* cited by examiner

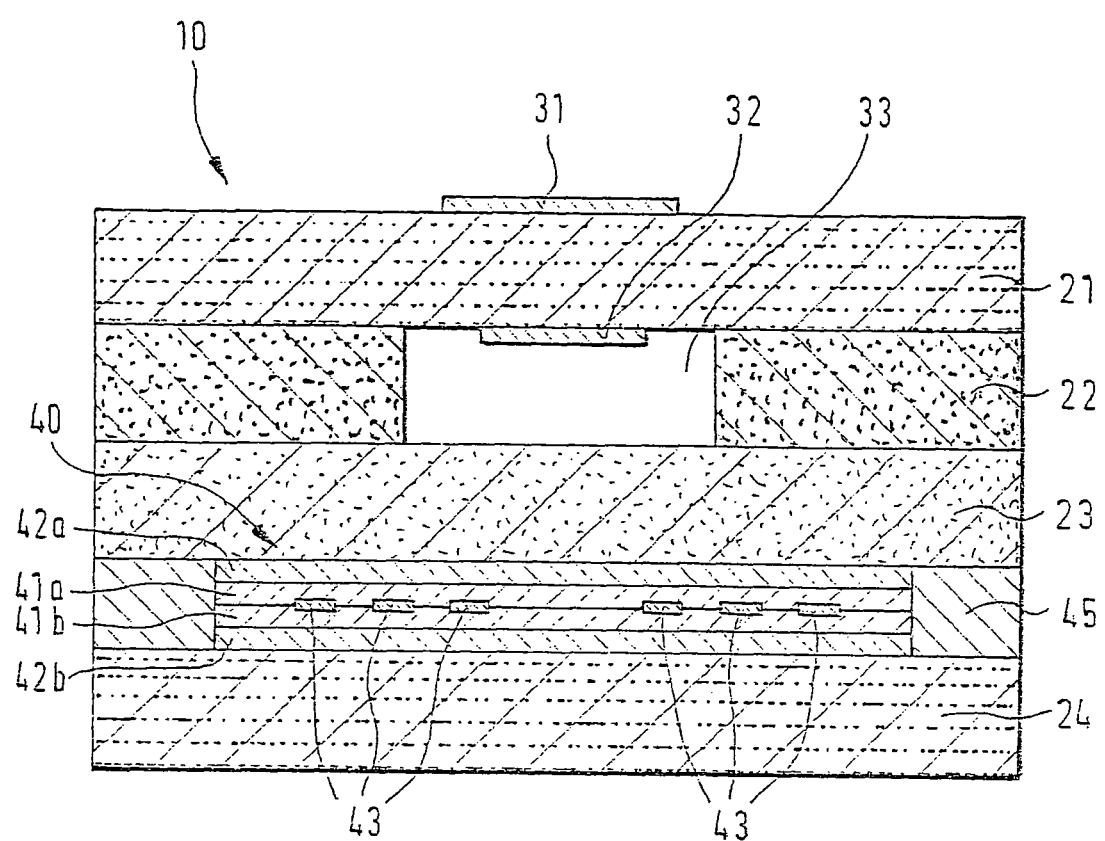

GAS SENSOR HEATING DEVICE INSULATION

FIELD OF THE INVENTION

The present invention is directed to a heating device.

BACKGROUND INFORMATION

Such a heating device is known, for example, from German Published Patent Application No. 198 34 276 for heating a sensor element which is used in a gas sensor for exhaust gas analysis in internal combustion engines. The sensor element has solid electrolyte layers and electrodes, as well as a heating device having a stratified design. The heating device is situated on a solid electrolyte layer or between one solid electrolyte layer and another solid electrolyte layer. The heating device contains a heating element made up, for example, of an electrical resistor layer and an insulator in which the heating element is embedded. The insulator is essentially made of aluminum oxide. The insulator electrically insulates the heating element against the solid electrolyte layers and the electrodes, as well as against electron and ion conduction, so that the function of the sensor element is not impaired by the operation of the heating device.

The heating device is manufactured by applying a lower insulator layer, the heating element, and an upper insulator layer to a green foil, i.e., an unsintered ceramic foil, using thin layer or thick layer technology. The green foil including the printed-on heating device is subsequently laminated together with other green foils onto which electrodes may be printed, for example, and is sintered.

The insulator is often porous. The porosity of the insulator is achieved by adding a pore former prior to sintering. During sintering, the pore former is burned away, so that a porous structure is obtained. The porosity is adjusted via the amount of pore former, for example, carbon glass, which is added.

German Published Patent Application No. 198 53 601 furthermore describes a broadband lambda probe for determining the oxygen concentration in exhaust gases of internal combustion engines. The sensor element of the probe includes a heating device, which is electrically insulated from a solid electrolyte layer by an insulator. The insulator contains a mixture of aluminum oxide, barium oxide, and/or strontium oxide to prevent leak currents.

The disadvantage of such a sensor element is that the sintering characteristics, in particular sintering shrinkage, of the solid electrolyte layer and the adjacent barium and/or strontium-containing insulator are distinctly different. The thermal expansion coefficients of the insulator and the solid electrolyte layer are also different. The poor bonding of the insulator to the solid electrolyte layer results in cracks, for example, in the event of rapid temperature changes, which impair the functionality of the sensor element.

SUMMARY OF THE INVENTION

The heating device according to the present invention having the characterizing features of the independent claim has the advantage over the related art that the leak currents exiting the heating element are largely prevented and the risk of cracks in the heating element due to poor bonding to a solid electrolyte foil adjacent to the heating device is greatly reduced.

For this purpose, the heating element is surrounded by a first insulator, which is adjoined by a second insulator. The first insulator has a higher barium and/or strontium and/or calcium content (expressed in weight percentage) than the second insulator. The sintering characteristics and thermal expansion coefficient of the second insulator are therefore between those of the first insulator and the solid electrolyte layer.

The measures recited in the dependent claims permit advantageous refinements of the heating device defined in the independent claim.

It has been found particularly advantageous that the first insulator contains barium and/or strontium and/or calcium in a proportion of 3 wt. % to 15 wt. % and the second insulator contains barium and/or strontium and/or calcium in a proportion of 0 wt. % to 4 wt. %. The first and second insulators have aluminum oxide as an additional constituent. Barium and strontium contents are to be understood in this document as the sum of barium content and strontium content, both expressed in weight percentages (similarly for other combinations of barium, strontium, and calcium).

The layer thickness of the first insulator is advantageously 5 µm to 40 µm, and the layer thickness of the second insulator 5 µm to 20 µm. The first insulator may have one upper and one lower layer, between which the heating element is situated. The layer thickness of the first insulator is understood in this case as the sum of the layer thicknesses of the upper and lower layers of the first insulator. Likewise, the second insulator may have an upper and a lower layer, between which the first insulator and the heating element are provided. The layer thickness of the second insulator in this case refers to the individual layer thicknesses of the upper or lower layer of the second insulator. The indicated layer thicknesses are advantageous, because layer thicknesses greater than 5 µm largely prevent impairment of the insulating effects due to defective spots, and layer thicknesses of less than 40 µm for the first insulator and 20 µm for the second insulator largely prevent the formation of cracks.

When moisture is able to penetrate the heating element of the heating device, for example, via a contact, cracks may occur in the insulator. The formation of cracks is prevented particularly effectively if the first insulator has a higher porosity than the second insulator.

BRIEF DESCRIPTION OF THE DRAWING

The FIGURE shows a cross section of an exemplary embodiment of a planar sensor element having a heating device according to the present invention.

DETAILED DESCRIPTION

The FIGURE shows as an exemplary embodiment of the present invention a planar, stratified sensor element 10 having first, second, third, and fourth oxygen ion-conducting solid electrolyte layers 21, 22, 23, 24 made of zirconium oxide stabilized with yttrium oxide. A first electrode 31, which is exposed to a measuring gas, is situated on first solid electrolyte layer 21 on the outside of sensor element 10. Furthermore, a second electrode 32, which is exposed to a reference gas in a reference channel 33, is situated on the side of first solid electrolyte layer 21 facing away from first electrode 31. Reference channel 33 is introduced into second solid electrolyte layer 22 and is connected to a reference gas atmosphere (not shown) situated outside sensor element 10.

First and second electrodes 31, 32 and first solid electrolyte layer 21 form an electrochemical cell, which is operated potentiometrically, for example. If the measuring gas and the reference gas have different oxygen partial pressures, a Nernst voltage is generated between first and second electrodes 31, 32, via which the oxygen partial pressure in the measuring gas may be determined.

Since the ion conductivity of the solid electrolytes is a function of temperature, sensor element 10 must be heated to a uniform temperature. For this purpose, a heating device 40, laterally surrounded by a sealing frame 45, is provided between third and fourth solid electrolyte layers 23, 24.

Heating device 40 has a heating element 43, which is made of a platinum-containing resistor layer. Heating element 43 is embedded between an upper and a lower layer 41a, 41b of a first insulator 41. First insulator 41, together with heating element 43, is embedded between an upper and a lower layer 42a, 42b of a second insulator 42. First and second insulators 41, 42 contain aluminum oxide as their main constituent. The manufacture of such insulators 41, 42 is essentially known to those skilled in the art and is not illustrated in detail.

In a first variant of the exemplary embodiment, first insulator 41 in sintered sensor element 10 has barium in a proportion of 9 wt. % in addition to aluminum oxide. Second insulator 42 does not contain barium. The sum of the layer thicknesses of upper and lower layers 41a, 41b of first insulator 41 is 25 µm. The layer thickness of the upper and lower layers 42a, 42b of second insulator 42 is 10 µm each.

In a second variant of the exemplary embodiment, barium may be entirely or partly replaced by strontium and/or calcium.

The heating device according to the present invention may also be used in other sensor types, such as in a broadband lambda probe or an NOx sensor. In a broadband lambda probe, such as described in German Published Patent Application No. 198 53 601 or in "Automotive Electronics Handbook," Ed. 1999, Publisher: Ronald K. Jurgen, McGraw-Hill, Section 7 and the documents cited therein, the sensor element contains an electrochemical Nernst cell and an electrochemical pump cell. Oxygen is pumped by the pump cell into a measuring gas space or from the measuring gas space in such a way that an oxygen partial pressure of lambda=1 is obtained in the measuring gas space. For this purpose, the pump cell is adjusted via the Nernst cell which measures the oxygen partial pressure in the measuring gas space. The oxygen partial pressure in the exhaust gas may be determined from the pump flow in the pump cell. As a result of the heating device according to the present invention, interference and leak currents either into the Nernst cell or into the pump cell of a broadband lambda probe may be reduced and thus the accuracy of the broadband lambda probe may be considerably enhanced.

What is claimed is:

1. A heating device for a sensor element of a gas sensor, comprising:
   at least one solid electrolyte layer;
   a heating element that includes an electrical resistor layer;
   a first insulator in which the heating element is fully embedded; and
   a second insulator including two additional insulator layers, which are respectively adjacent to opposing side of the first insulator and located between the first insulator and the at least one solid electrolyte layer, the first insulator and the second insulator electrically insulating the heating element from the at least one solid electrolyte layer, wherein:
   a content of at least one of barium, strontium, and calcium expressed in weight percentages of the first insulator being greater than that of the second insulator, and
   the at least one of barium, strontium and calcium is present only in the first insulator and the second insulator.

2. The heating device as recited in claim 1, wherein:
the heating device is for use in an exhaust gas analysis of an internal combustion engine.

3. The heating device as recited in claim 1, wherein:
the first insulator and the second insulator contain aluminum oxide.

4. The heating device as recited in claim 1, wherein:
the content of at least one of barium, strontium, and calcium of the first insulator is 3 wt. % to 15 wt. %.

5. The heating device as recited in claim 1, wherein:
the content of at least one of barium, strontium, and calcium of the first insulator is 7 wt. %.

6. The heating device as recited in claim 1, wherein:
the content of at least one of barium, strontium, and calcium of the second insulator is 0 wt. % to 4 wt. %.

7. The heating device as recited in claim 1, wherein:
a layer thickness of the first insulator is 5 µm to 40 µm.

8. The heating device as recited in claim 1, wherein:
a layer thickness of the first insulator is 25 µm.

9. The heating device as recited in claim 1, wherein:
a layer thickness of the second insulator is 5 µm to 20 µm.

10. The heating device as recited in claim 1, wherein:
a layer thickness of the second insulator is 10 µm.

11. The heating device as recited in claim 1, wherein:
the barium is added to at least one of the first insulator and the second insulator prior to sintering in the form of a barium compound.

12. The heating device as recited in claim 11, wherein:
the barium compound includes one of $BaCO_3$, $BaSO_4$, $Ba(NO_3)_2$ and $BaO_2$.

13. The heating device as recited in claim 1, further comprising:
at least one further insulator having a content of at least one of barium, strontium, and calcium that is between that of the first insulator and the second insulator, the at least one further insulator being provided between the first insulator and the second insulator.

14. The heating device as recited in claim 1, wherein:
a porosity of the first insulator is higher than that of the second insulator.

15. The heating device as recited in claim 1, wherein:
the heating device is laterally surrounded by a sealing frame made of an ion-conducting material.

* * * * *